`US007001607B1`

(12) United States Patent
Menz et al.

(10) Patent No.: US 7,001,607 B1
(45) Date of Patent: Feb. 21, 2006

(54) ARTIFICIAL TEAR REPLACEMENT SOLUTION

(75) Inventors: Dirk-Henning Menz, Diedorf (DE); Joachim Dresp, München (DE); Martin Winter, Bremen (DE)

(73) Assignee: Bausch & Lomb Incorporated, Rochester, NY (US)

( * ) Notice: Subject to any disclaimer, the term of this patent is extended or adjusted under 35 U.S.C. 154(b) by 556 days.

(21) Appl. No.: 10/049,558

(22) PCT Filed: Jun. 30, 2000

(86) PCT No.: PCT/EP00/06109

§ 371 (c)(1),
(2), (4) Date: Jun. 26, 2002

(87) PCT Pub. No.: WO01/12159

PCT Pub. Date: Feb. 22, 2001

(30) Foreign Application Priority Data

Aug. 14, 1999 (DE) ................................ 199 38 668

(51) Int. Cl.
*A61K 31/74* (2006.01)
*A61F 2/00* (2006.01)

(52) U.S. Cl. ................ 424/427; 424/78.04; 514/772.4; 514/914; 514/944

(58) Field of Classification Search ............. 424/78.02, 424/427; 514/755, 756, 832, 743, 772.4, 514/914, 944
See application file for complete search history.

(56) References Cited

U.S. PATENT DOCUMENTS 5,480,914 A * 1/1996 Meadows .................... 514/743
5,573,757 A * 11/1996 Riess et al. .............. 424/78.02

FOREIGN PATENT DOCUMENTS

| EP | 0112658 A2 | 7/1984 |
| EP | 0288659 A1 | 11/1988 |
| WO | WO 95/09606 | 4/1995 |

* cited by examiner

*Primary Examiner*—Thurman K. Page
*Assistant Examiner*—Micah-Paul Young
(74) *Attorney, Agent, or Firm*—Martin Fleit; Paul D. Bianco; Fleit Kain Gibbons Gutman Bongini & Bianco P.L.

(57) ABSTRACT

A tear replacement solution that contains at least one water-soluble fluorosurfactant, water and a non-polar component, preferably in gel form, and a method for the external treatment for the eye of an mammal by applying the tear replacement solution to the eye, preferably by placing in the conjunctival sac.

14 Claims, No Drawings

ARTIFICIAL TEAR REPLACEMENT SOLUTION

BACKGROUND OF THE INVENTION

1. Field of the Invention

The invention relates to a tear substitute for the external treatment of the eye.

2. Prior Art

Tear substitutes are used in the treatment of diseases of the eye, such as common keratoconjunctivitis sicca (so-called "dry eye"). Dry eye can be the result of different causes. The most frequent causes include reduction in tear production in the elderly, rheumatic or internal diseases (such as polyarthritis, diabetes and thyroid disease), diseases in which antibodies are raised against the body's own physiological substances (Sjörgren's disease, Lupus erythematodes, sclerodermia), skin diseases, hormonal changes, neuroparalysis (such as after a stroke, defective position of the eyelid, decortication of tear glands), ingestion of certain drugs (such as β blockers, birth control pill, soporifics and tranquilizers), nutritional deficiency, climatic influences (heat, dry environmental air, season, air conditioners), environmental pollution (ozone, dust, solvent vapors, etc.), working in front of monitors, and chronic use of vessel contracting eyedrops (so-called whiteners). Furthermore, such eye diseases are also caused, but less frequently, by autoimmune diseases, diseases of the hematopoietic system, local eye diseases such as inflammation and trauma of the tear glands or hereditary diseases. The resulting dysfunctions impair or prevent the formation of a normal tear film, which has an exceedingly complicated structure in its natural form. There are essentially three components which participate in the formation of the tear film:

An internal mucin layer which covers the epithelial surface, followed by a middle aqueous layer, and a thin, external lipid layer. The mucin layer here functions as an adhesive component for the wetting of the cornea. The aqueous component moisturizes the cornea and it has a cleaning and protective function. The lipid component prevents evaporation of the aqueous component and prevents a quick runoff of the tear film.

Only an intact tear film can guarantee the full functionality of the eye surface over time, and, in addition to the mentioned defects, properties which reduce abrasion, antibacterial properties, and the oxygen supply of the cornea can be of importance. The above-mentioned components of tears are continuously produced. The formation of a thin tear film over the cornea occurs spontaneously with each blink of the eyelid, as, during the downward movement of the upper lid, the external lipid layer of the tear film is compressed between the lid margins, where the aqueous layer essentially remains in its position. As soon as a part of the production of the tear components is interrupted or disturbed, or there is a mechanical obstacle to the formation of the tear film as a result of the blinking of the eyelid, corresponding complaints arise from, for instance the so-called sand grain effect to massive visual disorders, which in extreme cases, can lead to blindness as a result of irreversible damage to the cornea.

As there are a multitude of possible causes of "dry eye" and as the problem of the tear film [formation] is complex, a multitude of treatment agents are known from the state of the art. In this context, examples are the patents EP 698 388, DE 195 11 322, DE 43 03 818, EP 801 948, WO 97/45102, and WO 96/33695.

In the above-mentioned patents, descriptions are essentially provided of treatment agents which, as a result of introduction into the conjunctival sac, replace one or more missing components of natural tear film. The replacement is here carried out using substances which, having an appropriate retention time, take over the protective and abrasion-reducing functions, and possess the same or at least similar properties as the components to be substituted. The treatment agent which is commercially available under the trade name "Liposic," for example, constitutes an attempt to duplicate all the natural tear components in a so-called three-dimensional tear.

The liquid treatment agents which are known from the state of the art, however, all present the drawback of having a relatively short residence time on the cornea. As a result, the treatment agent must be introduced at regular intervals into the eye, which can be very inconvenient and unpleasant for the patient. In the known gel form treatment agents, this drawback is at least partially avoided. However, in the case of gel form treatment agents, it was shown to be difficult to supply sufficient oxygen to the cornea.

In the patents EP 089 815 and EP 112 658, ophthalmological treatment agents for lubrication and protection of the eye surface are proposed which contain a perfluorocarbon or a substituted derivative thereof. The substantial advantages compared to conventional treatment agents that are mentioned are here the immiscibility with water and the high gas dissolution capacity, particularly for oxygen.

Because of the known high oxygen dissolution capacity of fluorocarbons, the treatment agent described in the above patents is said to guarantee a sufficient oxygen supply for the cornea. In addition, because of the high density of the perfluorocarbons, a long residence time on the cornea is said to be possible because the compounds are said to become enriched due to their high specific weight. Moreover, it is claimed that, because of the insolubility of the treatment agent in water, the use of preservatives could be omitted.

However, the drawbacks of these perfluorocarbon-containing treatment agents are that an intact mucin layer and sufficient secretion of lipids must be guaranteed to allow sufficient functionality of the agent on the cornea. Additional drawbacks result from impaired vision as a result of the formation of streaks, as well as the risk of obstructing the tear drainage ducts, caused by the immiscibility of the perfluorocarbons with water. Moreover, the immiscibility of perfluorocarbon and water, as well as the large interfacial tension between aqueous and perfluorocarbon-containing areas lead to the formation of diffusion barriers, which prevents a sufficient supply [of oxygen] to the cornea.

In addition, different forms of fluorogels are known from the state of the art, which were also proposed for medicinal applications. From U.S. Pat. No. 5,573,757 and EP 340 079 as well as WO 97/03644, polyaphron gels are known whose structure is stabilized by fluorinated surfactants. The structure and the properties of polyaphron gels are described, for example, in Chapter 8 of Foams and Biliquid Foams-Aphrons, F. Sebba, John Wiley, 1987.

Fluorogels as such, in general, present a pronounced viscoelasticity. These substances therefore are not suitable for an extraocular treatment of eye diseases, because the absence of a pronounced property of film formation does not allow an even distribution and wetting of the cornea.

Therefore, the problem of the present invention is to provide a tear substitute which is tolerated over the long term, which allows even wetting of the cornea, which presents a long retention time on the eye surface, and which guarantees the supply of oxygen and water-soluble nutrients to the cornea.

SUMMARY OF THE INVENTION

This problem is solved by using and/or applying to a person's or animal's eye a tear substitute for external treatment of the eye, characterized in that it contains at least one water-soluble fluorinated surfactant, water and a nonpolar component. In particular, the nonpolar component is a fluorocarbon or a silicone oil.

DETAILED DESCRIPTION OF PREFERRED EMBODIMENTS

There will now be described in detail the present invention and how the novel compositions of the present invention are formulated, and how they are used by applying to a person's or animal's eye. Essentially the tear substitute composition of the invention contains at least one water-soluble fluorinated surfactant, water and a nonpolar component. In particular, the nonpolar component is a fluorocarbon or a silicone oil. The fluorocarbon is chosen from the group comprising perfluoro compounds, partially fluorinated compounds having the general formula $R_F R_H$ or $R_F R_H R_F$, as well as, fluoro oligomers of the type $(R_F)_x R_H$, or a mixture thereof.

The tear substitute according to one aspect of the invention is characterized in that it is in the form of a gel and presents a polyaphron structure. The fluorinated surfactant is prepared according to the general formula:

$$R_F\text{---}R_{pol}$$

where $R_F$ represents a linear or branched perfluoroalkyl group having more than 5 carbon atoms and $R_{pol}$ represents a polar hydrocarbon residue which comprises at least one functional group chosen from the series:

CO—NH(R), CO—NH(R)$_2$, COO—, COOR, SO$_3$—, SO$_2$—N(R)$_2$, CH$_2$—O—, R, PO$_2$H, PO$_3$H$_2$, where R represents an alkyl.

The tear substitute according to the invention is characterized in that the molecular weight of the fluorinated surfactant is greater than 400 g/mol, and the surface tension of the fluorinated surfactant in an aqueous solution is less than 30 mNm. Further, according to the invention, the tear substitute is characterized in that the concentration of the fluorinated surfactant is less than critical micellar formation concentration, preferably less than 0.1%, and the concentration of the fluorocarbon is greater than 60 wt %, preferably greater than 90 wt %.

In a more specific aspect of the invention, the tear substitute is characterized in that the water-soluble fluorinated surfactant presents at least 6 completely fluorinated carbon atoms.

The tear substitute according to the invention is characterized in that it presents a refractive index of from 1.334 to 1.338.

As taught by the invention, the tear substitute is characterized in that the tear substitute on the cornea forms a thin film. The sum of the surface tension of the tear substitute and the interfacial tension between the tear substitute and the surface of the eye is smaller than the surface tension of the surface of the eye. When applied to an eye, the gel of tear substitute liquefies at least partially irreversibly under the effect of shearing stresses. It is preferred that the tear substitute be introduced into the conjunctival sac where the tear substitute forms a gel-form reservoir, a part of which liquefies during each blink of the eyelid. The liquefied portion of the tear substitute on the cornea forms a thin film.

One of the essential foundations of the present invention consists of the knowledge that a preparation which contains water, a nonpolar component and a water-soluble fluorinated surfactant, evenly wets smooth hydrophobic surfaces as soon as the preparation is in liquid form. The mechanism which effects the even distribution of the liquid preparation as a thin film on the smooth surface is the spreading of the immiscible components of the preparation according to the invention on top of each other, or on the hydrophilic or hydrophobic surface.

As a result, with the tear substitutes according to the invention, it is possible to achieve film formation from a water-containing preparation on the hydrophobic cornea. The formation of the thin film on the cornea here occurs as a result of blinking of the eyelid, as in natural tear formation. In this context, it is particularly the combination of hydrophilic, hydrophobic and fluorophilic properties, resulting from the structure of the fluorinated surfactants, which is used for the wetting of the cornea surface. By maintaining certain concentrations of the fluorinated surfactants it is possible, in addition, to adjust the surface and interfacial tensions of the components of the invention in such a manner that an optimal film formation and sufficient supply of oxygen to the cornea are possible.

The formation of thin films on the cornea surface leads to high residence capacities for the preparations and at the same time to the absence of prevention of tear secretion, mucus production and secretion of the marginal eyelid glands. Additionally, the resulting films prevent adhesion of the lid. In addition, the special surface properties of the preparation allow their passage, at the end of the residence time, into the natural tear drainage ducts without obstructing them. In this manner, the preparations according to the invention can take over the abrasion reducing and wetting functions of natural tear film without causing undesired side effects such as obstructed tear drainage ducts.

As a result of the combination of the components of the tear substitute according to the invention, it is possible to benefit from the advantages of the individual components without having to take into account any drawbacks.

The wetting properties of surfactants are well known, and they are used in many industrial processes. However, it is precisely these intrinsically advantageous properties which are the cause of their poor biocompatibility, which is reflected above all in dysfunctions in cell membranes. Therefore, the use of surfactant-containing substances in medical applications is strongly limited because of toxic behavior. Thus, for example, incompatibilities of oxygen-transporting emulsions can be explained by the effect of the surfactants which they contain. In particular, it appears that the use of surfactant-containing substances as tear substitutes is ruled out, because the function of the natural tear film is decisively effected by the surface-modifying properties of the lipids, and the latter react particularly sensitively to additives of other surfactant substances.

However, by the combination of the components of the tear substitute according to the invention, the surface active effect of the surfactants was, nevertheless, unexpectedly exploited, without impairment of the function of the surfactant compounds present in the natural tear film. The fluorinated surfactants used according to the invention, in this context, are characterized, in contrast to other known surfactants, by an improved biocompatibility. Fluorinated surfactants by themselves offer an improved biocompatibility, compared to nonfluorine-containing emulsifiers, combined with an unusual surface activity.

In addition, the damaging effects of the fluorinated surfactants in the preparations according to the invention are further repressed by the effects of the nonpolar components. This is achieved by the fixing of the fluorinated surfactants in the nonpolar matrix, resulting in a lowering of the surface tension of the aqueous components, without destroying the conditions which are caused by the natural surfactant compounds of the tear film. In this context, one exploits the fact that the interactions of the fluorinated surfactants with the nonpolar components are stronger than with the lipophilic components of the eye surface.

In this manner, the known surfactant properties of surfactants can be exploited for extraocular applications. In combination with the properties of water and the nonpolar matrix, the fluorinated surfactants provide the film-forming properties of the preparations according to the invention, and thus they allow an even thin-film wetting of the cornea.

As nonpolar components, fluorocarbons or silicone oil are particularly suited. If fluorocarbons are used as nonpolar components, the known advantageous properties of these substances, such as the high oxygen solubility and the lubricating and protecting function, can be exploited. As a result of the oxygen-transporting properties of the fluorocarbons, the cornea is sufficiently supplied with oxygen without impairing vision due to irregular layer thicknesses or milky emulsions, and without the formation of barrier layers between the hydrophobic cornea and the lipophobic fluorocarbons, which prevent oxygen transfer. In this context, it should be emphasized that fluorocarbon does not need a carrier (as, for example, in EP 089 815), rather it acts itself as a carrier for the fluorinated surfactants.

The formation of thin films as a result of the blinking of the eyelid and the spreading of the nonmiscible components not only leads to good gliding properties of the tear substitute according to the invention, in addition, because of the resulting fine distribution, it also is responsible for an increased residence duration on the surface. The latter effect is further supported by the fact that the thin film spontaneously seeks the lowest possible layer thicknesses, while the chosen surface and boundary properties at the same time act against rupturing of the films. By an appropriate selection of the components of the tear substitute, the surface tension of the tear substitute and the interfacial tension between the tear substitute and eye surface can be adjusted in such a manner that the sum of the two magnitudes is greater than the surface tension of the surface of the eye. This allows, in particular, improved film formation as a result of spreading on the eye surface. The film-like layer structures produced by spreading can take over the function of the natural tear film, where the cornea is wetted and protected without the need to hydrophilize the cornea surface.

The sliding properties and the residence duration can be further improved if the tear substitute according to the invention is first in the form of a polyaphron gel. It was found that such gels made of the components according to the invention decompose to the liquid condition as a result of the high shear stresses generated during blinking of the eyelid. This decomposition is irreversible as soon as the polyaphron structure is completely destroyed in the entire volume of the gel. It was shown that, as a result of shearing stresses, produced, for example, during the blinking of an eyelid, a certain volume of the gel is released as a result of irreversible liquefaction, and the liquefied portion of the gel is then evenly distributed on smooth surfaces due to spreading of the immiscible components, in the form of a thin film. Advantageously, the gel-form tear substitute is introduced into the conjunctival sac, where it forms a gel-form reservoir. During each blinking of the eyelid, a portion of the gel is liquefied and then it is finely and evenly distributed, in the form of a thin film, over the cornea surface.

With the described preparations according to the invention, the requirements for a tear substitute are successfully and excellently met. In this context, it should be mentioned, in particular, that although individual components intrinsically contribute important functions, it is only the combination of the individual components which allows the combination of the excellent properties of the fluorinated surfactants and the nonpolar components.

In this context, it is particularly the combination of the oxygen-transporting properties and the uptake capacity for water-soluble nutrients with the properties of high transparence and good film formation, which is of crucial importance. In addition to the replacement of functions such as wetting, reduction of abrasion, supply of nutrients and oxygen, additional properties of the preparations can also be used, such as the lipophobic properties of the preparations, leading to a reduction in the deposition of sebum, and the absence of sticking of the eyelid. An additional advantage results from the preservative properties of the nonpolar components of which not all the manufacturing steps must be carried out under sterile conditions. This means the preparations can be sterilized after the manufacture, for example, by treatment at 121° C. for 15 min in autoclaves, where the use of additional preservatives can be omitted.

The following examples should further explain the manufacture and the use of preparations according to the invention.

EXAMPLE 1

0.1 g Fluowet® (trade name, the company Clariant) OTL, 0.9 g water and 99 g perfluorophenanthrene (having a surface tension of $\sigma=19$ mNm) are homogenized, sterilized at 121° C. for 15 min, and then applied by means of syringe to a mirror and distributed, where the surface is wetted by an even, nonrupturing film.

EXAMPLE 2

Polyaphron gels are prepared by known methods from tetraethylpiperazinium salt of perfluorooctanoic acid ($\sigma=15.9$ mNm; 0.1 g), balanced salt solution (BSS); 0.9 g and perfluorophenanthrene ($\sigma=19$ mNm; 99 g) or perfluoroalkylethanol oxethylate ($\sigma=19$ mNm; 0.1 g) BSS (0.9 g) and perfluorophenanthrene ($\sigma=19$ mNm; 99 g), and sterilized at 121° C. for 15 min in the autoclave. The gel-form preparations were filled into syringes and investigated by a Draize test. No irritations occurred during the Draize test. Even two weeks after application of the gel, the tear secretion, mucus production or secretion of the lid margin glands in rabbits was not impaired. Even after continuation of daily treatment for 16 weeks, no signs of incompatibility were observed.

EXAMPLE 3

A preparation prepared according to Example 1 is applied to the eyes of rabbits. A short time after application, a known treatment agent for enlarging the pupils is applied. It was observed that the pupil-enlarging agent loses its effect as soon as a thin film of the tear substitute according to the invention has formed on the cornea. This observation serves as a demonstration of the capacity of the preparation according to the invention to form thin closed films over the cornea, as with the natural tear. In addition, this example shows that the preparations according to the invention have a protective function, by preventing water-containing or water-soluble substance from coming in contact with the eye surface as soon as a film has formed on the cornea.

EXAMPLE 4

From a 10% solution of perfluorooctanoic acid tetraethylpiperazinium salt (having surface tension σ=15.9 mNm) in water and highly purified silicone oil 1000 mPas, a gel is produced by foaming the aqueous solution and introduction of the silicone oil. After sterilization at 121° C. for 15 min, this preparation is applied to a water-loaded surface. Spontaneous spreading occurs.

What is claimed is:

1. Method for the treatment of an eye of a mammal, the eye having a conjunctival sac comprising the steps of:
   a. preparing a sterile polyaphron gel comprising at least one water-soluble fluorinated surfactant in a concentration lower than critical micellae formation, water and one homopolar component in an amount greater than 60% by weight selected from the group consisting of partially fluorinated fluorocarbon compounds of the general formula $R_F R_H$, $R_F R_H R_F$, fluorocarbon oligomers of the type $(R_F)_x R_H$, silicone oil, and mixtures thereof;
   b. introducing the sterile polyaphron gel into the conjunctival sac of the eye to form a gel-like reservoir whereupon at each blink of the eye, a portion of the sterile polyaphron gel irreversibly liquefies under the effect of the shear forces caused by the blink, extrudes from the conjunctival sac and spreads over the cornea of the eye as a thin liquid film functioning as a tear substitute.

2. Method in accordance with claim 1, wherein the fluorinated surfactant is of the general formula $$R_F\text{—}R_{POL}$$

whereby $R_F$ is a linear or branched perfluoroalkyl group having more than 5 carbon atoms and Rpol is a polar hydrogen residue comprising at least one functional group selected from the series CO—NH(R), CO—NH(R)$_2$, COO—, COOR, SO$_3$, SO$_2$—N(R)$_2$, CH$_2$—O—R, PO$_2$H, PO$_3$H whereby R is an alkyl.

3. Method in accordance with claim 1, wherein the molecular mass of the fluorinated surfactant is greater than 400/lmol, and the surface tension of the fluorinated surfactant in aqueous solution is less than 30 m/Nm.

4. Method in accordance with claim 1, wherein the concentration of the fluorinated surfactant is lower than 0.1% and the concentration of fluorocarbons is greater than 90 weight percent.

5. Method in accordance with claim 1, wherein the water-soluble fluorinated surfactant has at least 6 fully fluoridated carbon atoms.

6. Method in accordance with claim 1, wherein the sterile polyaphron gel has a refraction index of 1.334 to 1.338.

7. Method in accordance with claim 1, wherein the sum of the surface tension of the sterile polyaphron gel and the interfacial tension between the sterile polyaphron gel and the surface of the eye is smaller than the surface tension of the surface of the eye.

8. A sterile polyaphron gel comprising at least one water-soluble fluorinated surfactant in a concentration lower than critical micellae formation, water and one homopolar component in an amount greater than 60% by weight selected from the group consisting of partially fluorinated fluorocarbon compounds of the general formula $R_F R_H$, $R_F R_H R_F$, fluorocarbon oligomers of the type $(R_F)_x R_H$, silicone oil, and mixtures thereof; said sterile polyaphron gel being adapted for introduction into the conjunctival sac of an eye of a mammal to form a gel-like reservoir whereupon at each blink of the eye, a portion of the sterile polyaphron gel will liquefy irreversibly under the effect of the shear forces caused by the blink, extrude from the conjunctival sac and spread over the cornea of the eye as a thin liquid film functioning as a tear substitute.

9. A sterile polyaphron gel in accordance with claim 8, wherein the fluorinated surfactant is of the general formula $$R_F\text{—}R_{POL}$$

whereby $R_F$ is a linear or branched perfluoroalkyl group having more than 5 carbon atoms and Rpol is a polar hydrogen residue comprising at least one functional group selected from the series CO—NH(R), CO—NH(R)$_2$, COO—, COOR, SO$_3$, SO$_2$—N(R)$_2$, CH$_2$—O—R, PO$_2$H, PO$_3$H whereby R is an alkyl.

10. A sterile polyaphron gel in accordance with claim 8, wherein the molecular mass of the fluorinated surfactant is greater than 400/lmol, and the surface tension of the fluorinated surfactant in aqueous solution is less than 30 m/Nm.

11. A sterile polyaphron gel in accordance with claim 8, wherein the concentration of the fluorinated surfactant is lower than 0.1% and the concentration of fluorocarbons is greater than 90 weight percent.

12. A sterile polyaphron gel in accordance with claim 8, wherein the water-soluble fluorinated surfactant has at least 6 fully fluoridated carbon atoms.

13. A sterile polyaphron gel in accordance with claim 8, wherein the sterile polyaphron gel has a refraction index of 1.334 to 1.338.

14. A sterile polyaphron gel in accordance with claim 8, wherein the surface tension of the sterile polyaphron gel is adjusted such that the sum of the surface tension of the sterile polyaphron gel and the interfacial tension between the sterile polyaphron gel and the surface of the eye is smaller than the surface tension of the surface of the eye.

* * * * *